United States Patent
Reid, Jr. et al.

(10) Patent No.: US 10,130,416 B2
(45) Date of Patent: Nov. 20, 2018

(54) LIMITED REUSE ABLATION NEEDLES AND ABLATION DEVICES FOR USE THEREWITH

(75) Inventors: William O. Reid, Jr., Longmont, CO (US); Darion R. Peterson, Boulder, CO (US); Gene H. Arts, Berthoud, CO (US); John R. Vantuno, Denver, CO (US); Casey M. Ladtkow, Westminster, CO (US)

(73) Assignee: Covidien LP, Mansfield, MA (US)

( * ) Notice: Subject to any disclaimer, the term of this patent is extended or adjusted under 35 U.S.C. 154(b) by 1046 days.

(21) Appl. No.: 13/460,398

(22) Filed: Apr. 30, 2012

(65) Prior Publication Data

US 2013/0289558 A1    Oct. 31, 2013

(51) Int. Cl.
*A61B 18/18*    (2006.01)
*A61B 18/14*    (2006.01)
(Continued)

(52) U.S. Cl.
CPC ...... *A61B 18/1477* (2013.01); *A61B 18/1815* (2013.01); *A61B 90/98* (2016.02);
(Continued)

(58) Field of Classification Search
CPC ......... A61B 18/00; A61B 18/18; A61B 17/00; A61B 2017/00004; A61B 1/00057;
(Continued)

(56) References Cited

U.S. PATENT DOCUMENTS

D223,367 S    4/1972    Kountz
D263,020 S    2/1982    Rau, III
(Continued)

FOREIGN PATENT DOCUMENTS

CN    1103807 A    6/1995
DE    390937 C    3/1924
(Continued)

OTHER PUBLICATIONS

Koyle et al., "Laparoscopic Palomo Varicocele Ligation in Children and Adolescents" Pediatric Endosurgery & Innovative Techniques, vol. 6, No. 1, 2002.
(Continued)

*Primary Examiner* — Eric D. Bertram
*Assistant Examiner* — Elizabeth K So (57) ABSTRACT

A surgical instrument includes a reusable component and a limited-use component releasably engagable with the reusable component. The reusable component includes a detecting member and is configured to connect to a source of energy. The limited-use component is transitionable from a first state to a second state. The detecting member is configured to detect a response of the limited-use component for determining the state of the limited-use component. Energy is permitted to be supplied to the limited-use component when it is determined that the limited-use component is disposed in the first state. Energy is inhibited from being supplied to the limited-use component when it is determined that the limited-use component is disposed in the second state.

4 Claims, 3 Drawing Sheets

(51) Int. Cl.
  *A61B 18/00* (2006.01)
  *A61B 90/00* (2016.01)
  *A61B 90/98* (2016.01)

(52) U.S. Cl.
  CPC .............. *A61B 2018/00023* (2013.01); *A61B 2018/00577* (2013.01); *A61B 2018/00607* (2013.01); *A61B 2018/00988* (2013.01); *A61B 2090/0803* (2016.02); *A61B 2090/0807* (2016.02); *A61B 2090/0809* (2016.02); *A61B 2090/0814* (2016.02)

(58) Field of Classification Search
  CPC ............ A61B 1/00059; A61B 1/00062; A61B 1/00064; A61B 1/00066; A61B 1/00071; A61B 8/4494; A61B 2018/0019; A61B 2018/00958; A61B 2018/00988; A61B 2090/0814; A61B 2560/0266; A61B 2560/0276; A61B 2560/028; A61B 2560/0285; A61N 1/375
  See application file for complete search history.

(56) References Cited

U.S. PATENT DOCUMENTS

| | | |
|---|---|---|
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van de Peer |
| 5,448,042 A | 9/1995 | Robinson et al. |
| D424,693 S | 5/2000 | Pruter |
| D424,694 S | 5/2000 | Tetzlaff et al. |
| D425,201 S | 5/2000 | Tetzlaff et al. |
| 6,221,070 B1 | 4/2001 | Tu et al. |
| D449,886 S | 10/2001 | Tetzlaff et al. |
| D457,958 S | 5/2002 | Dycus et al. |
| D457,959 S | 5/2002 | Tetzlaff et al. |
| D487,039 S | 2/2004 | Webster et al. |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| D564,662 S | 3/2008 | Moses et al. |
| 7,367,973 B2 | 5/2008 | Manzo et al. |
| D576,932 S | 9/2008 | Strehler |
| 7,435,112 B1 | 10/2008 | Miller et al. |
| D594,736 S | 6/2009 | Esjunin |
| D594,737 S | 6/2009 | Kelly et al. |
| D606,203 S | 12/2009 | Husheer et al. |
| D613,412 S | 4/2010 | DeCarlo |
| D634,010 S | 3/2011 | DeCarlo |
| 8,540,709 B2* | 9/2013 | Allen .............................. 606/41 |
| 8,998,938 B2* | 4/2015 | Seto et al. .................... 606/167 |
| 2003/0199735 A1 | 10/2003 | Dickopp et al. |
| 2004/0267254 A1 | 12/2004 | Manzo et al. |
| 2007/0055219 A1 | 3/2007 | Whitman et al. |
| 2009/0065565 A1 | 3/2009 | Cao |
| 2011/0137323 A1 | 6/2011 | Malkowski et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4303882 A1 | 8/1994 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 0979658 A1 | 2/2000 |
| EP | 1 159 926 A2 | 12/2001 |
| EP | 1829495 A1 | 9/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |

(56) References Cited

FOREIGN PATENT DOCUMENTS

| WO | 2004/096032 A1 | 11/2004 |
|---|---|---|
| WO | 2010/035831 A1 | 4/2010 |

OTHER PUBLICATIONS

LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.

Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.

(56) References Cited

OTHER PUBLICATIONS

European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.

(56) References Cited

OTHER PUBLICATIONS

European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSureTM Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSureTM Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSureTM Vessel Sealing System in Urologic Cancer Surger" Grand Rounds in Urology 1999, vol. 1, Issue 4, pp. I 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Venous Complex" Sales/Product Literature 2000.
Esterline, "Light Key Projection Keyboard", Advanced Input Systems, <http://www.advanced-input.com/lightkey> (2002).
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.

(56) References Cited

OTHER PUBLICATIONS

Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. Decarlo.
U.S. Appl. No. 13/083,256, filed Apr. 8, 2011, Joseph D. Brannan.
U.S. Appl. No. 13/113,736, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Examination Report for corresponding Australian Application No. 2013257269 dated Nov. 18, 2016.
European Search Report EP 13164267 dated Aug. 21, 2013.
European Examiantion Report issued in Appl. No. EP 16 197 560.2-1115 dated Apr. 9, 2018 (6 pages).
Extended European Search Report issued in Appl. No. EP 16 197 560.2-1659 dated Jun. 2, 2017 (9 pages).

* cited by examiner

LIMITED REUSE ABLATION NEEDLES AND ABLATION DEVICES FOR USE THEREWITH

BACKGROUND

Technical Field

The present disclosure relates to surgical instruments and, more particularly, to ablation devices including disposable needles configured for single-use or a limited amount and/or number of uses.

Background of Related Art

Energy-based tissue treatment is well known in the art. Various types of energy (e.g., electrosurgical, ultrasonic, microwave, cryogenic, thermal, laser, etc.) are applied to tissue to achieve a desired result, e.g., to cut, ablate, coagulate, and/or seal tissue.

Electrosurgery involves the application of radio frequency (RF) energy to a surgical site to cut, ablate, coagulate, and/or seal tissue. In monopolar electrosurgery, a source or active electrode, which is typically part of the surgical instrument held by the surgeon, delivers RF electrical current from a generator to tissue, while a patient return electrode is placed remotely from the active electrode to carry the current back to the generator.

In tissue ablation electrosurgery, for example, the RF energy may be delivered to targeted tissue by a probe or needle. More specifically, in use, the needle is typically advanced through tissue to a desired position either prior to or during application of energy to tissue. After repeated use, these needles may become dull, bent, or otherwise deformed and, consequently, may become more difficult to place and operate upon subsequent use. As such, ablation devices have been developed which include replaceable needles, thus allowing the needle to be replaced after one or more uses without requiring replacement of the entire device (e.g., the handpiece).

SUMMARY

As used herein, the term "distal" refers to the portion that is being described which is further from a user, while the term "proximal" refers to the portion that is being described which is closer to a user. Further, to the extent consistent with one another, any of the aspects described herein may be used in conjunction with any of the other aspects described herein.

In accordance with aspects of the present disclosure, a surgical instrument is provided. The surgical instrument generally includes a reusable component and a limited-use component. The reusable component includes a detecting member and is configured to connect to a source of energy. The limited-use component is releasably engagable with the reusable component and is transitionable from a first state to a second state. The detecting member is configured to detect a response of the limited-use component for determining the state of the limited-use component. Energy is permitted to be supplied to the limited-use component when it is determined that the limited-use component is disposed in the first state. On the other hand, energy is inhibited from being supplied to the limited-use component when it is determined that the limited-use component is disposed in the second state.

In one aspect, the surgical instrument includes an ablation device having a reusable handle assembly and a limited-use needle assembly that is releasably engagable with the handle assembly.

In another aspect, the detecting member is configured to detect a natural frequency of the limited-use component. The limited-use component defines one or more first natural frequencies corresponding to the first state and one or more second natural frequencies corresponding to the second state.

In another aspect, the limited-use component includes an expandable member. The expandable member is configured to transition from a contracted condition, wherein the limited-use component defines the first natural frequency, to an expanded condition, wherein the limited-use component defines the second natural frequency, upon transitioning of the limited-use member from the first state to the second state.

In still another aspect, the detecting member includes an optical sensor configured to sense one or more optical characteristics exhibited by a portion (or the entire) of the limited-use component. The portion (or the entire) of the limited-use component exhibits one or more first optical characteristics corresponding to the first state and one or second optical characteristics corresponding to the second state.

In yet another aspect, the portion (or the entire) of the limited-use component includes a color-change member. The color-change member is configured to exhibit a first color when the limited-use component is disposed in the first state and to exhibit a second color when the limited-use component is disposed in the second state.

In still yet another aspect, the limited-use component is transitioned from the first state to the second state upon application of fluid thereto, heating to a pre-determined temperature, application of electrical energy thereto, and/or application of chemicals thereto.

In another aspect, the reusable component includes control circuitry including a memory. The control circuitry is configured to receive a response from the detecting member and to compare the response to one or more stored response stored in the memory for determining the state of the limited-use component.

In accordance with aspects of the present disclosure, a surgical instrument is provided. The surgical instrument includes a reusable component and a limited-use component. The reusable component includes a detecting member and is configured to connect to a source of energy. The limited-use component is transitionable from a first state, wherein the limited-use component defines a first natural frequency, to a second state, wherein the limited-use component defines a second natural frequency. The detecting member is configured to detect the natural frequency of the limited-use component for determining the state of the limited-use component. Energy is permitted to be supplied to the limited-use component when it is determined that the limited-use component is disposed in the first state. On the other hand, energy is inhibited from being supplied to the limited-use component when it is determined that the limited-use component is disposed in the second state.

In one aspect, the detecting member includes an acoustic transmitter and receiver. The transmitter is configured to emit an excitation signal within the limited-use component and the acoustic receiver is configured to receive a standing wave response from the limited-use component that corresponds to a natural frequency of the limited-use component.

In another aspect, the limited-use component includes an expandable member disposed therein. The expandable member is expandable from a contracted condition to an expanded condition to transition the limited-use component from the first state to the second state.

In another aspect, the expandable member is transitionable from the contracted condition to the expanded condition upon application of fluid thereto, heating to a pre-determined temperature, application of electrical energy thereto, and/or application of chemicals thereto.

In yet another aspect, the surgical instrument includes an ablation device including a reusable handle assembly and a limited-use needle assembly releasably engagable with the handle assembly.

In still another aspect, the reusable component includes control circuitry including a memory. The control circuitry is configured to receive a response from the detecting member and to compare the response to one or more stored response stored in the memory for determining the state of the limited-use component.

A surgical instrument provided in accordance with aspects of the present disclosure includes a reusable component and a limited-use component. The reusable component includes an optical sensor and is configured to connect to a source of energy. The limited-use component is releasably engagable with the reusable component and is transitionable from a first state, wherein a portion (or the entire) of the limited-use component exhibits a first optical characteristic, to a second state, wherein the portion (or the entire) of the limited-use component exhibits a second optical characteristic. The optical sensor is configured to detect the optical characteristic of the portion (or the entire) of the limited-use component for determining the state of the limited-use component. Energy is permitted to be supplied to the limited-use component when it is determined that the limited-use component is disposed in the first state. On the other hand, energy is inhibited from being supplied to the limited-use component when it is determined that the limited-use component is disposed in the second state.

In one aspect, the surgical instrument includes an ablation device including a reusable handle assembly and a limited-use needle assembly releasably engagable with the handle assembly.

In another aspect, the portion (or the entire) of the limited-use component includes a color-change member that is configured to exhibit a first color when the limited-use component is disposed in the first state and to exhibit a second color when the limited-use component is disposed in the second state.

In yet another aspect, the limited-use component is transitioned from the first state to the second state upon application of fluid thereto, heating to a pre-determined temperature, application of electrical energy thereto, and/or application of chemicals thereto.

In still yet another aspect, the reusable component includes control circuitry including a memory. The control circuitry is configured to receive a response from the optical sensor and to compare the response to one or more stored responses stored in the memory for determining the state of the limited-use component.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
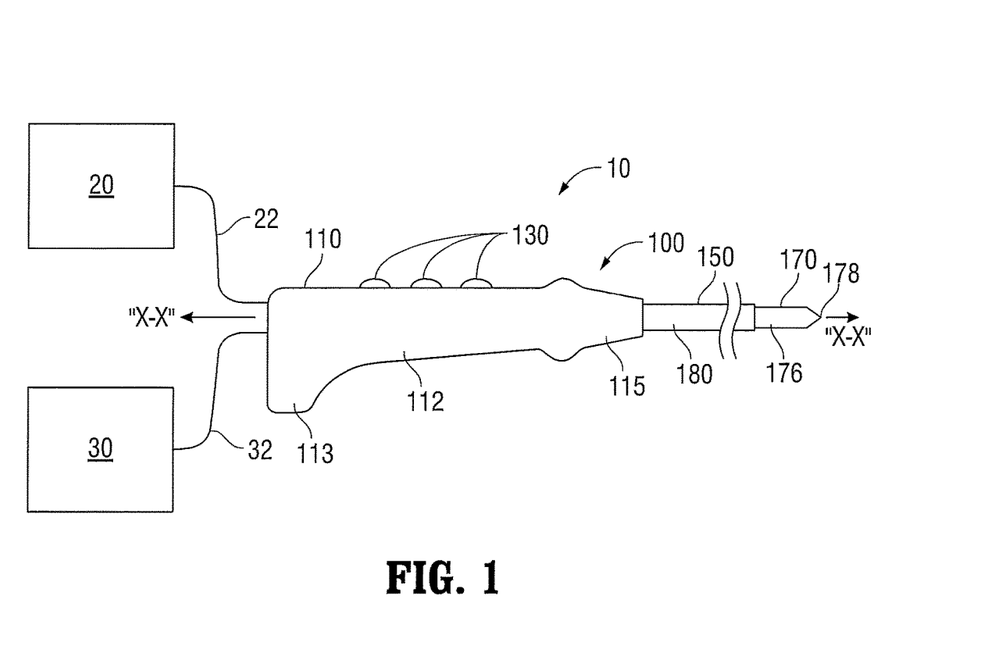
FIG. 1 is a side view of an electrosurgical ablation system provided in accordance with the present disclosure.
Figure 2:
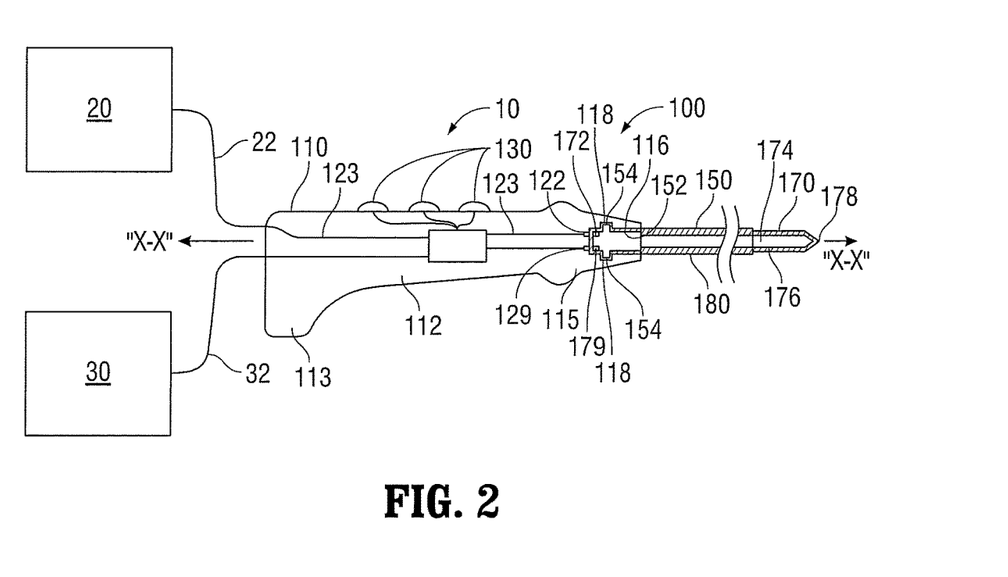
FIG. 2 is a longitudinal, cross-sectional view of the electrosurgical ablation system of FIG. 1.

Referring initially to FIGS. 1-2, an ablation system provided in accordance with the present disclosure is shown generally designated by reference numeral 10. Although ablation system 10 is shown configured as an RF-ablation system 10, the present disclosure is equally applicable for use with microwave ablation systems, or any other suitable surgical system including single-use or limited-use disposable components. Obviously, different considerations apply depending on the particular device and/or system used; however, the novel aspects with respect to inhibiting or limiting re-use of the needle (or other component) remains generally consistent regardless of the particular type of device and/or system used. For the purposes herein, ablation system 10 is generally described.

Continuing with reference to FIGS. 1-2, ablation device 100 of ablation system 10 generally includes a handle assembly 110 and a needle electrode assembly 150 releasably engagable with and extending from handle assembly 110. Although only one needle electrode assembly 150 is shown, it is envisioned that additional needle electrode assemblies, either similar to or different from needle electrode assembly 150, may be provided for releasable engagement with handle assembly 110. As such, a desired needle electrode assembly may be selected and engaged to handle assembly 110, depending on a particular purpose and/or to replace a "spent" needle, e.g., a used needle, in the case of single-use needles, or a needle that has reached its usage limit and/or its maximum number of uses, in the case of limited use needles.

Handle assembly 110 includes a housing 112 which may be ergonomically or otherwise configured to facilitate the grasping and manipulation of housing 112 by a user to position needle electrode assembly 150 as desired. Housing 112 is formed from an insulative material and defines proximal and distal ends 113, 115, respectively. Proximal end 113 of housing is configured to receive lines 22, 32 from an energy source, e.g., generator 20, and cooling fluid source 30, respectively, for supplying energy and cooling fluid, respectively, to needle electrode assembly 150. Distal end 115 of housing 112 defines an engagement recess 116 configured to receive proximal end 152 of needle electrode assembly 150 therein for engaging needle electrode assembly 150 and handle assembly 110 to one another. More specifically, engagement recess 116 of housing 112 defines one or more notches 118 therein that are configured to engage protrusions 154 extending outwardly from proximal end 152 of needle electrode assembly 150 upon insertion of needle electrode assembly 150 into engagement recess 116 of housing 112 for releasably mechanically engaging needle electrode assembly 150 and handle assembly 110 to one another. Other releasable engagement mechanisms, e.g., snap-fit engagements, threaded-engagements, friction-fit engagements, etc., are also contemplated.

With continued reference to FIGS. 1-2, handle assembly 110 further includes one or more electrical contacts 122 disposed on the base surface of engagement recess 116 that are configured to electrically couple to one or more corresponding electrical contacts 172 positioned at proximal end 152 of needle electrode assembly 150 upon mechanical engagement of handle assembly 110 and needle electrode assembly 150 to one another, thereby establishing electrical communication between handle assembly 110 and needle electrode assembly 150 upon mechanical engagement of handle assembly 110 and needle electrode assembly 150 to one another. One or more wires 123 extending through housing 112 of handle assembly 110 ultimately couple contacts 122 to line 22, which extends proximally from housing 112 of handle assembly 110, ultimately coupling to generator 20. As such, power and/or control signals may be transmitted between generator 20 and needle electrode assembly 150 via the one or more pairs of electrically-coupled contacts 122, 172. In particular, one or more pairs of contacts 122, 172 may be configured for establishing a conductive path for transmission of energy between generator 20 and needle electrode assembly 150. As such, upon activation, energy can be transmitted from generator 20 to needle electrode assembly 150, e.g., via line 22, wires 123, and contacts 122, 172, and, ultimately, conducted through tissue to ablate or otherwise treat tissue. As an alternative to external generator 20, it is contemplated that generator 20 be incorporated into handle assembly 110, thus providing a hand-held ablation device 100.

Another pair of contacts 122, 172 may be utilized for identifying or verifying the identification of the particular type of needle electrode assembly 150 engaged with handle assembly 110. As can be appreciated, this feature helps ensure that an acceptable needle electrode assembly 150 has been engaged to handle assembly 110 and/or that the proper energy delivery and control parameters for the particular needle electrode assembly 150 engaged with handle assembly 110 are provided by generator 20. Additionally or alternatively, the same or a different pair of contacts 122, 172 may be utilized to indicate the number of times that the particular needle electrode assembly 150 engaged with handle assembly 110 has been used. Further, the operation of cooling fluid source 30 may also be at least partially dependent upon the particular type of needle electrode assembly 150 detected. Thus, identifying information for the particular type of needle electrode assembly 150 engaged to handle assembly 110 may be relayed to and utilized by cooling fluid source 30 for controlling the supply of cooling fluid to needle electrode assembly 150 in accordance therewith. Other configurations of contact(s) or similar features for establishing electrical communication and electrical energy transmission between handle assembly 110 and needle electrode assembly 150 are also contemplated.

Needle electrode assembly 150 defines a longitudinal axis "X-X" and includes an electrically-conductive needle 170 defining a hollow interior 174, an insulative sleeve 180 (or coating) disposed about a portion of the external surface of needle 170, and, as mentioned above, one or more electrical contacts 172 configured to permit electrical coupling of needle 170 to handle assembly 110 upon mechanical engagement of needle electrode assembly 150 and handle assembly 110 to one another.

Proximal end 152 of needle electrode assembly 150 is configured for insertion into engagement recess 116 of housing 112 of handle assembly 110 and includes a pair of outwardly-extending protrusions 154 (or other suitable complementary structure) configured to releasably engage notches 118 defined within engagement recess 116 of handle assembly 110 to releasably engage needle electrode assembly 150 within engagement recess 116 of handle assembly 110.

Continuing with reference to FIGS. 1-2, needle 170 extends distally from engagement recess 116 of housing 112 of handle assembly 110 to distal end 176 thereof, which defines a distal tip 178 configured to facilitate the penetration of tissue while minimizing the risk of hemorrhage from the puncture tract, although other distal tip configurations are also contemplated. Needle 170 is formed from an electrically-conductive material of which at least distal end 176 is exposed. An insulating sleeve 180, or coating of material, surrounds the remaining portion of needle 170 that extends distally from engagement recess 116. With at least distal end 176 of needle 170 exposed, energy, e.g., RF energy, can be delivered from needle 170 to surrounding tissue to treat, e.g., ablate, tissue.

As mentioned above, an energy source, e.g., generator 20, is provided for providing power and/or control signals to needle electrode assembly 150 via line 22, one or more wires 123, and one or more pairs of contacts 122, 172. Further, a cooling fluid source 30 is provided for providing cooling fluid to needle electrode assembly 150. Cooling fluid source 30 provides cooling fluid, via line 32 (which includes both inflow and outflow lines), such that cooling fluid supplied by the cooling fluid source 30 may be circulated through hollow interior 174 of needle 170 to maintain needle electrode assembly 150 in a relatively cooled state during the application of energy to tissue. Cooperating valves 179, 129 of needle electrode assembly 150 and handle assembly 110, respectively, may be provided to facilitate the passage, e.g., inflow and outflow, of cooling fluid between cooling fluid source 30 and hollow interior 174 of needle 170, although other configurations are also contemplated. Circulation of the cooling fluid may be established through the use of a pump (not shown) or other suitable mechanism disposed within housing 112 of handle assembly 110, or the pump (not shown) may be externally disposed.

In operation, ablation device 100, lead by distal tip 178 of needle 170, is inserted into an operative site such that exposed distal end 176 of needle 170 of ablation device 100 is positioned adjacent to or within a target tissue to be treated, e.g., ablated. A return pad or return electrode (not shown) may, at this point or prior to, be operatively-adhered to or connected to the patient. With exposed distal end 176 of needle 170 in position, energy, e.g., RF energy, is delivered from generator 20 to needle 170 and is conducted from exposed distal end 176 of needle 170 through the target tissue, ultimately to be collected by the return electrode (not shown). As can be appreciated, an effective amount of energy at an effective energy level and for an effective duration of time is delivered to tissue to achieve the desired result, e.g., to treat the target tissue. To this end, one or more control switches 130 may be provided on handle assembly 110 for controlling the supply of energy to needle 170, or, alternatively, the supply of energy may be automatically or manually controlled by generator 20.

Either prior to or simultaneously with the delivery of electrosurgical energy to needle 170, the cooling fluid provided by cooling fluid source 30 may be circulated through hollow interior 174 of needle 170 to withdraw heat from needle 170, thus maintaining needle 170 in a relatively cooled state during use. The delivery of cooling fluid to hollow interior 174 of needle 170 may likewise be controlled by one or more control switches 130 disposed on handle assembly 110, or via cooling fluid supply 30 itself.

At the completion of the procedure, needle electrode assembly 150 may be disengaged from handle assembly 110 and discarded, in those embodiments where needle electrode assembly 150 is configured as a single-use component or where needle electrode assembly 150 has reached its usage limit or maximum number of uses, or may be sterilized for re-use, in those embodiments where needle electrode assembly 150 has yet to reach its usage limit or maximum number of uses. Handle assembly 110 is configured as a reusable component and, thus, is sterilizable for re-use, although handle assembly 110 may also be configured as a disposable component.

Turning now to FIGS. 3A-3B, 4, 5, and 6A-6B, various different embodiments of ablation devices including needle electrode assemblies similar to needle electrode assembly 150 (FIGS. 1-2) and handle assemblies similar to handle assembly 110 (FIGS. 1-2) are described hereinbelow. Each of the ablation devices includes one or more single-use or limited use features for inhibiting re-use or limiting the use of the needle electrode assembly. Any of the ablation devices described hereinbelow may include any or all of the features of ablation device 100 (FIGS. 1-2), described above, or any of the other ablation devices described herein.

Figure 3A:
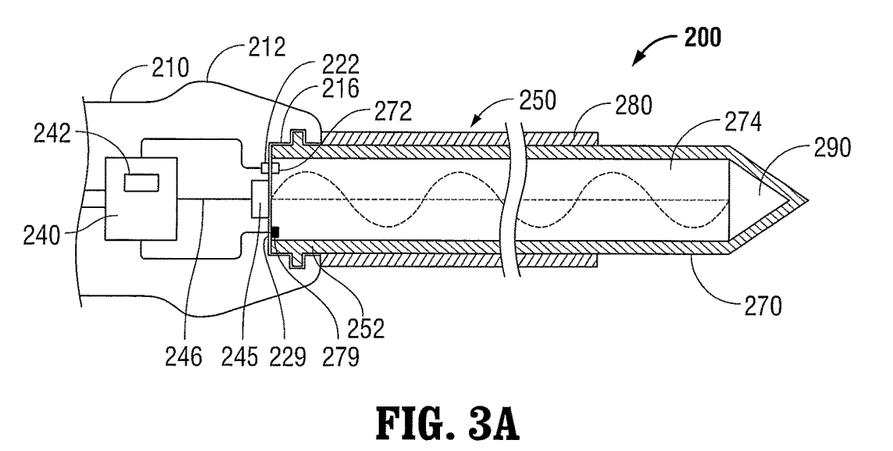
FIG. 3A is a longitudinal, cross-sectional view of another ablation device provided in accordance with the present disclosure and shown in a usable condition.
Figure 3B:
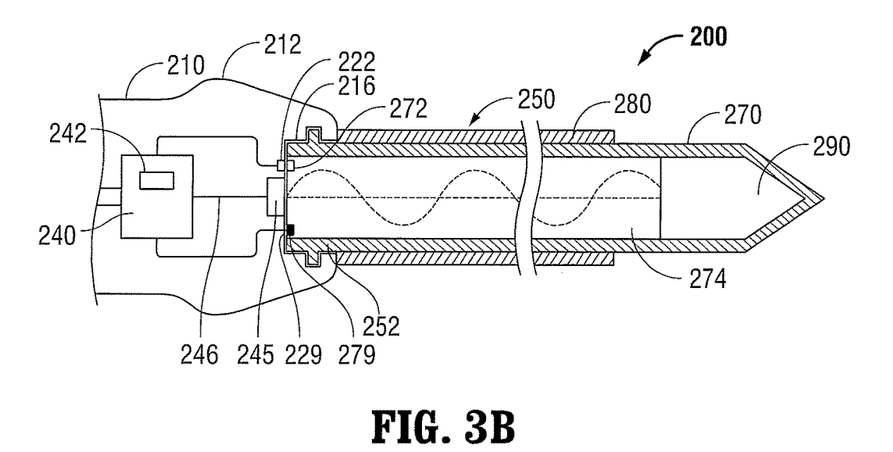
FIG. 3B is a longitudinal, cross-sectional view of the ablation device of FIG. 3A shown in a spent condition.

Referring to FIGS. 3A-3B, ablation device 200 is shown generally including a handle assembly 210 and a needle electrode assembly 250 releasably engagable with handle assembly 210. Handle assembly 210 includes a housing 212 defining an engagement recess 216 for releasably engaging proximal end 252 of needle electrode assembly 250 therein, similarly as described above with respect to ablation device 100 (FIGS. 1-2). Housing 212 of handle assembly 210 is further configured to couple to an energy source, e.g., generator 20 (FIG. 1), and a cooling fluid source, e.g., cooling fluid source 30 (FIG. 1), respectively, for supplying energy and cooling fluid, respectively, to needle electrode assembly 250.

One or more electrical contacts 222 of handle assembly 210 are configured to electrically couple to one or more corresponding electrical contacts 272 of needle electrode assembly 250 upon mechanical engagement of handle assembly 210 and needle electrode assembly 250 to one another, thereby establishing electrical communication between handle assembly 210 and needle electrode assembly 250 for transmitting power and/or control signals between generator 20 (FIG. 1), control circuitry 240 of handle assembly 210, and needle electrode assembly 250. Cooperating valves 279, 229 of needle electrode assembly 250 and handle assembly 210, respectively, on the other hand, facilitate the passage, e.g., inflow and outflow, of cooling fluid between the cooling fluid source 30 (FIG. 1) and hollow interior 274 of needle 270 of needle electrode assembly 250.

Needle 270 of needle electrode assembly 250 is formed from an electrically-conductive material, defines a hollow interior 274, and includes an insulative sleeve 280 (or coating) disposed about a portion of the external surface of needle 270. Needle 270 of needle electrode assembly 250, as shown in FIGS. 3A-3B, further includes one or more expandable members 290, e.g., an expandable foam, gel, or other suitable expandable material, member, component, or assembly, disposed within hollow interior 274 of needle 270 towards the distal end thereof, although expandable member 290 may alternatively be disposed at any other suitable position within hollow interior 274 of needle 270. Expandable member 290 is configured to expand from a contracted condition, as shown in FIG. 3A, to an expanded condition, as shown in FIG. 3B. Needle 270, inclusive of expandable member 290, defines an initial, pre-determined natural frequency when expandable member 290 is disposed in the contracted condition. As will be described below, expandable member 290 is configured such that, when transitioned from the contracted condition to the expanded position, the natural frequency of needle 270 is detectably or measurably changed.

Expandable member 290 may be configured to expand from the contracted condition to the expanded condition upon contact with one or more fluids, e.g., cooling fluid; expandable member 290 may be temperature-sensitive, e.g., wherein expandable member 290 expands (and remains in the expanded state) upon heating to a pre-determined temperature; expandable member 290 may be chemically-sensitive, e.g., wherein expandable member 290 expands (and remains in the expanded state) upon contact with a particular chemical (or chemicals); expandable member 290 may be electrically-sensitive, e.g., wherein expandable member 290 expands (and remains in the expanded state) upon application of electrical energy thereto; expandable member 290 may be light-sensitive, e.g., wherein expandable member 290 expands via a photochemical reaction upon exposure to light; and/or expandable member 290 may otherwise be configured to selectively transition from the contracted condition (FIG. 3A) to the expanded condition (FIG. 3B). Further, expandable member 290 may be configured to transition through one or more intermediate conditions, e.g., expandable member 290 may be configured to transition from the contracted condition to an intermediate condition and, ultimately, from the intermediate condition to the expanded condition. Expandable member 290 may alternatively or additionally include time-sensitive features such that expandable member 290 is expanded from the contracted condition (FIG. 3A) to the expanded condition (FIG. 3B), for example, upon exposure to one or more fluids, a pre-determined temperature, etc., for a pre-determined amount of time.

As an alternative to expandable member 290, needle 270 may include a transformable material (not shown) disposed therein that is configured to contract, dissolve, disperse and/or otherwise transform upon contact with fluid(s), heating, application of chemical(s), application of electrical energy, application of light, and/or occurrence of any other suitable condition, thereby changing the natural frequency of needle 270. In fact, needle 270 may include any suitable material, member, component, or assembly disposed within hollow interior 274 thereof that is configured to transition from a first state to a second state upon occurrence of a particular condition whereby transitioning of the material, member, component, or assembly from the first state to the second state changes the natural frequency of needle 270.

With continued reference to FIGS. 3A-3B, handle assembly 210 further includes an acoustic transmitter/receiver 245 (although the transmitter and receiver may alternatively be separate components and/or any other suitable transmitter/receiver may be provided) disposed therein and positioned adjacent to engagement recess 216 such that, upon engagement of needle electrode assembly 250 and handle assembly 210 to one another, acoustic transmitter/receiver 245 is disposed in proximity to proximal end 252 of needle electrode assembly 250. Acoustic transmitter/receiver 245 is coupled via line 246 to control circuitry 240 of handle assembly 210 and/or to the control circuitry of generator 20 (FIGS. 1-2). Control circuitry 240 (and/or the control circuitry of generator 20 (FIGS. 1-2)) controls the signal emitted from the transmitter of acoustic transmitter/receiver 245 and analyzes the response received by the receiver of acoustic transmitter/receiver 245. As will be described below, the transmitter of acoustic transmitter/receiver 245 is configured to emit a pre-determined acoustic excitation signal, e.g., at the initial natural frequency of the needle 270 or a harmonic frequency there, into hollow interior 274 of needle 270, while the receiver of acoustic transmitter/receiver 245 is configured to detect the standing wave response, which is correlated to the natural frequency of the needle 270. The standing wave response detected by the receiver of acoustic transmitter/receiver 245 is transmitted to control circuitry 240 of handle assembly 210 (and/or the control circuitry of generator 20 (FIG. 1)), which analyzes the response. More specifically, control circuitry 240 of handle assembly 210 (and/or the control circuitry of generator 20 (FIG. 1)) may include a memory 242 configured to store one or more acceptable response values, e.g., in a look-up table of memory 242, for comparison to the response value corresponding to the standing wave response received by the receiver of acoustic transmitter/receiver 245 to determine whether use of needle electrode assembly 250 is permitted and, thus, to determine whether to supply electrical energy and/or cooling fluid to needle electrode assembly 250. The response values stored in memory 242 include at least those values corresponding to the natural frequency of needle 270 of electrode assembly 250 when expandable member 290 is disposed in the contracted condition (and any intermediate conditions), as well as the natural frequency of any other needle electrode assemblies approved for use with handle assembly 210.

The assembly and operation of ablation device 200 is described with reference to FIGS. 3A-3B. As shown in FIG. 3A, needle electrode assembly 250 is initially disposed in an unused condition (or in a condition wherein needle electrode assembly 250 includes at least one use or some amount of use time left) and, accordingly, expandable member 290 is disposed in the contracted condition. In preparation for use, needle electrode assembly 250 is inserted into recess 216 of housing 212 of handle assembly 210 to releasably engage handle assembly 210 and needle electrode assembly 250 to one another. Upon engagement of handle assembly 210 and needle electrode assembly 250 to one another, electrical contacts 222, 272 are likewise coupled to one another to electrically couple handle assembly 210 and needle electrode assembly 250 to one another, and valves 229, 279 are coupled to one another to permit the inflow/outflow of cooling fluid therebetween.

Automatically upon engagement, e.g., upon electrical coupling, of handle assembly 210 and needle electrode assembly 250 to one another, or upon manual user-activation, e.g., via actuation of one or more of control switches (similar to control switches 130 of ablation device 100 (FIG. 1)) disposed on handle assembly 250 and/or generator 20 (FIG. 1), the transmitter of acoustic transmitter/receiver 245 emits a pre-determined acoustic excitation signal into hollow interior 274 of needle 270 and the receiver of acoustic transmitter/receiver 245 subsequently detects the standing wave response. The detected response is then transmitted to control circuitry 240 of handle assembly 210 (and/or the control circuitry of generator 20 (FIG. 1)), which analyzes the response. More specifically, the response is converted into a corresponding response value, and the response valve is compared to the stored response value(s) stored in memory 242. If the response value is equal to (or within an acceptable range of) one of the stored response values, control circuitry 240 indicates that the needle electrode assembly 250 is accepted, e.g., via activating an LED (not shown) disposed on handle assembly 210 or providing an appropriate signal to generator 20 (FIG. 1) for display.

With respect to needle electrode assembly 250 when expandable member 290 is disposed in the contracted condition, as shown in FIG. 3A, the needle electrode assembly 250 is accepted since the natural frequency of needle 270 when expandable member 290 is disposed in the contracted condition is stored in memory 242. In embodiments where a set of stored responses is stored in memory 242, at least some of the stored responses may correspond to different types of needle electrode assemblies, thus allowing the use of multiple needle electrode assemblies with handle assembly 210. Such a feature also allows the use of only pre-approved needle electrode assemblies, e.g., those whose response value is stored in memory 242, thus inhibiting the use of incompatible or non-approved needle electrode assemblies. Further, in addition to accepting a particular needle electrode assembly, the particular stored response value matched to the needle electrode assembly may define certain use parameters for that particular needle electrode assembly. For example, different needle electrode assemblies may require different energy parameters, profiles, or algorithms, and/or may require various different cycles, controls, and/or algorithms of cooling fluid circulation. Thus, the acoustic transmitter/receiver 245 may be configured to both determine if the needle electrode assembly 250 engaged thereto is acceptable and, if so, identify the particular needle electrode assembly 250. Additionally or alternatively, in embodiments where contacts 222, 272 are utilized for identifying the needle electrode assembly 250, control circuitry 240 may cooperate with contacts 222, 272 and/or generator 20 (FIG. 1) such that, in order to accept the needle electrode assembly 250, the response value received must match the stored response value corresponding to that particular needle electrode assembly 250.

Thus, since expandable member 290 is disposed in the contracted condition (FIG. 3A) when needle electrode assembly 250 is engaged to handle assembly 210, needle electrode assembly 250 is accepted and approved for use. The use of ablation device 200 is similar to that of ablation device 100 (FIGS. 1-2) described above and, thus, will not be repeated here. After use, needle electrode assembly 250 is disengaged from handle assembly 210 and is discarded or sterilized for re-use. Handle assembly 210 is configured as a reusable component and, thus, is also sterilized for re-use.

As mentioned above, the circulation of cooling fluid through hollow interior 274 of needle 270, the supply of electrosurgical energy to needle 270, heat, chemicals, and/or any other suitable occurrence after a pre-determined number of uses, a pre-determined number of sterilizations and/or a pre-determine usage time, transitions expandable member 290 of needle electrode assembly 250 from the contracted condition, as shown in FIG. 3A, to the expanded condition, as shown in FIG. 3B.

Referring now to FIG. 3B, upon subsequent attempted use of needle electrode assembly 250, e.g., upon re-engagement of handle assembly 210 and needle electrode assembly 250 to one another with expandable member 290 in the expanded condition, the transmitter of acoustic transmitter/receiver 245 once again emits a pre-determined acoustic excitation signal into hollow interior 274 of needle 270 and the receiver of acoustic transmitter/receiver 245 detects the standing wave response, which is transmitted to control circuitry 240 of handle assembly 210 (and/or the control circuitry of generator 20 (FIG. 1)). However, with expandable member 290 of needle electrode assembly 250 now disposed in the expanded condition (and, thus, with natural frequency of needle 270 having changed), the response value thereof no longer matches the response value stored in memory 242. Accordingly, since the response value does not match any of the stored response values, needle electrode assembly 250 is rejected, inhibiting operation of needle electrode assembly, e.g., inhibiting the supply of electrical energy and/or cooling fluid to needle electrode assembly 250.

As can be appreciated in view of the above exemplary embodiment, acoustic transmitter/receiver 245, in conjunction with control circuitry 240 and expandable member 290, inhibits re-use of needle electrode assembly 250 when expandable member 290 is disposed in the expanded condition. Accordingly, depending on the configuration of expandable member 290, e.g., depending on what occurrence or occurrences effect transitioning of expandable member 290 to the expanded condition, use of needle electrode assembly 250 may be subsequently inhibited after a single use, a pre-determined number of uses, or a pre-determined amount of use time. Similarly, needle electrode assemblies which are not compatible with handle assembly 210, e.g., needle electrode assemblies whose natural frequencies are different and, thus, produce response values that do not match any of the response values stored in memory 242, are also rejected. Acoustic transmitter/receiver 245 and corresponding control circuitry 240 may also function inhibit use of a bent, deformed, or otherwise damaged needle electrode assembly, e.g., needle electrode assembly 450 (FIG. 5), similarly as will be described below with reference to FIG. 5.

Figure 4:
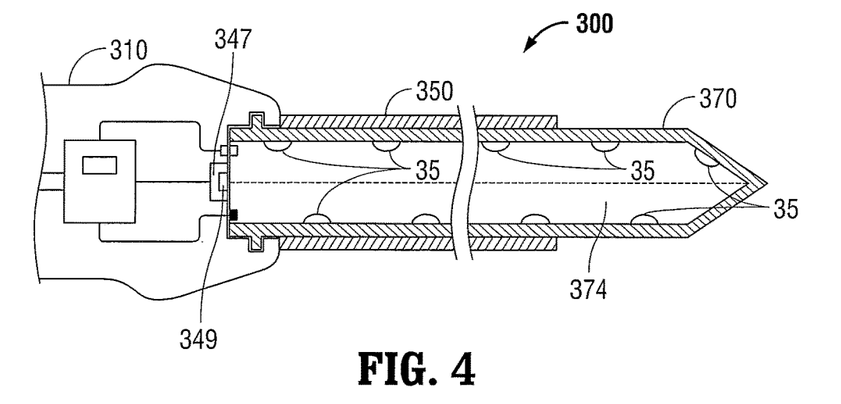
FIG. 4 is a longitudinal, cross-sectional view of another ablation device provided in accordance with the present disclosure and shown in a spent condition.

Turning now to FIG. 4, another embodiment of an ablation device 300 provided in accordance with the present disclosure is shown generally including a handle assembly 310 and a needle electrode assembly 350 releasably engagable with handle assembly 310. Ablation device 300 is similar to ablation device 200 (FIGS. 3A-3B) and, thus, only the differences therebetween will be described in detail hereinbelow. More specifically, ablation device 300 differs from ablation device 200 (FIGS. 3A-3B) in that needle 370 of needle electrode assembly 350 does not include an expandable member. Rather, through the use of a transmitter 347, in conjunction with a sufficiently sensitive receiver or sensor 349, e.g., a piezoelectric sensor, changes in the natural frequency of needle 370 after cooling fluid has been circulated therethrough can be detected, e.g., sensor 349 can detect changes in the response that result from natural frequency shifts due to the mass of cooling fluid 35 that remains inside hollow interior 374 of needle 370, even after needle 370 has seemingly be emptied. As such, sensor 349 can be used to accept only those needle electrode assemblies that have not had cooling fluid circulated therethrough, e.g., those that have yet to be used, while used needle electrode assemblies, e.g., needle electrode assembly 350, are rejected. Further, similarly as described above, sensor 349 may be used to only allow the use of pre-approved needle electrode assemblies, thus inhibiting the use of incompatible or non-approved needle electrode assemblies.

Figure 5:
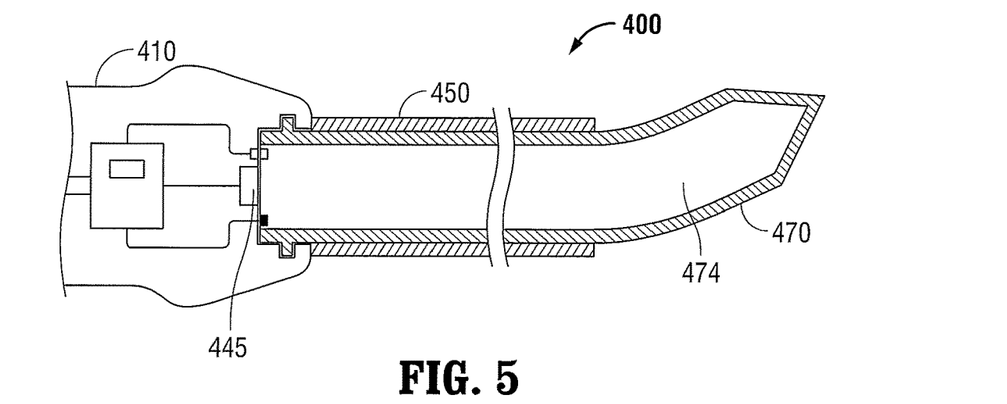
FIG. 5 is a longitudinal, cross-sectional view of another ablation device provided in accordance with the present disclosure and shown in a bent condition.

Referring to FIG. 5, ablation device 400 (similar to ablation devices 100 (FIGS. 1-2), 200 (FIGS. 3A-3B), and 300 (FIGS. 4A-4B)) is shown including a handle assembly 410 and a needle electrode assembly 450 releasably engagable therewith. Needle electrode assembly 450 includes a needle 470 that has suffered some damage. That is, needle 470 has been sufficiently bent and/or deformed such that the natural frequency of needle 470 has been changed. Accordingly, upon attempted use of needle electrode assembly 450, e.g., upon engagement of needle electrode assembly 450 with handle assembly 410, needle electrode assembly 450 is rejected. More specifically, upon engagement, transmitter/receiver 445 emits a pre-determined excitation signal into hollow interior 474 of needle 470, while the receiver or sensor of transmitter/receiver 445 detects the response, which is correlated to the natural frequency of the needle 470. However, since the natural frequency of needle 470 has been altered due to the damage inflicted on needle 470, the detected response is likewise altered sufficiently so as to be no longer recognizable. Thus, the needle electrode assembly 450 is rejected. As can be appreciated, the above-described feature inhibits the use of damaged needle electrode assemblies, even in instances where the needle electrode has yet to be used or has remaining uses or use time left. Although shown separately for exemplary purposes, needle electrode assembly 450 may be a needle electrode assembly configured for use with either of ablation devices 200, 300 (FIGS. 3A-3B and 4, respectively). In other words, needle 470 exemplifies a damaged needle attempted to be used with any of the ablation devices described herein.

Figure 6A:
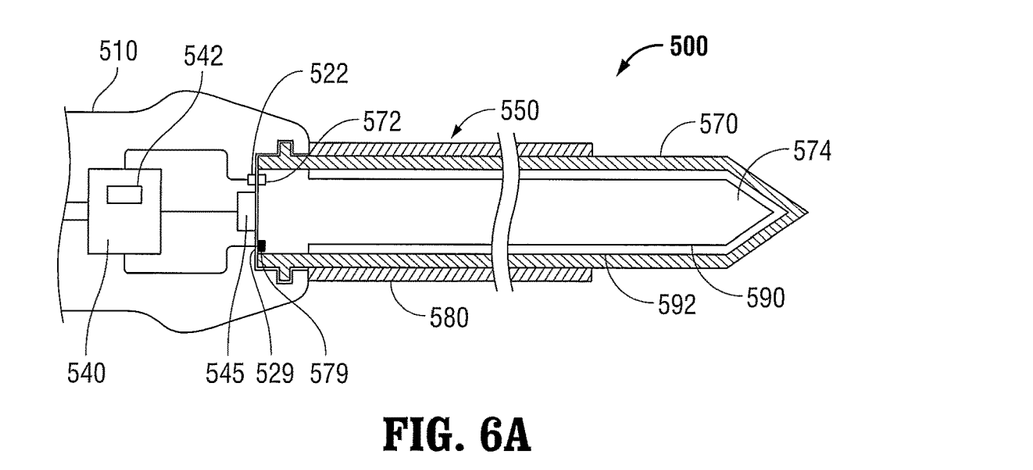
FIG. 6A is a longitudinal, cross-sectional view of another ablation device provided in accordance with the present disclosure and shown in a usable condition.
Figure 6B:
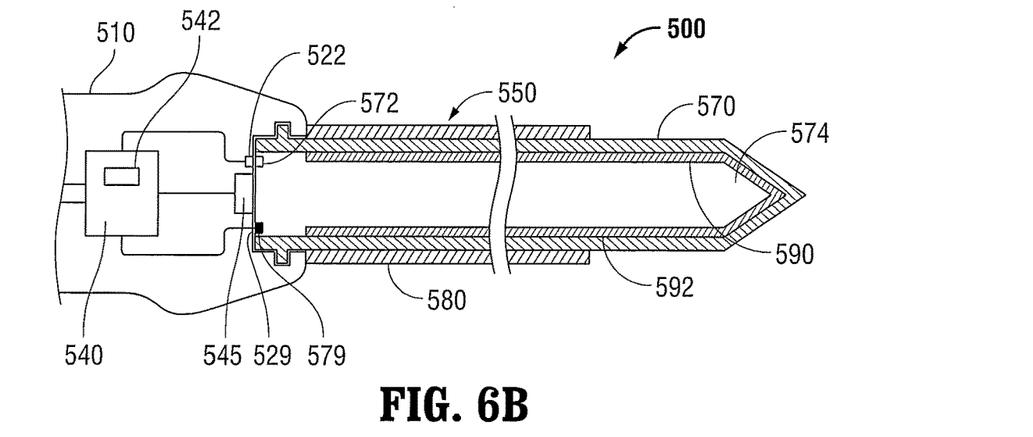
FIG. 6B is a longitudinal, cross-sectional view of the ablation device of FIG. 6A shown in a spent condition.

Turning now to FIGS. 6A-6B, another embodiment of an ablation device provided in accordance with the present disclosure is shown generally identified by reference numeral 500. Ablation device 500 is similar to ablation device 100 (FIGS. 1-2) and generally includes a handle assembly 510 and a needle electrode assembly 550 releasably engagable with handle assembly 510. Handle assembly 510 is configured to be coupled to an energy source, e.g., generator 20 (FIG. 1), and a cooling fluid source, e.g., cooling fluid source 30 (FIG. 1), respectively, for supplying energy and cooling fluid, respectively, to needle electrode assembly 550. Electrical contacts 522, 572 of handle assembly 510 and needle electrode assembly 550, respectively, establish electrical communication therebetween, similarly as described above. Further, cooperating valves 579, 529 of needle electrode assembly 550 and handle assembly 510, respectively, facilitate the passage of cooling fluid between the cooling fluid source 30 (FIG. 1) and hollow interior 574 of needle 570 of needle electrode assembly 550.

Needle 570 of needle electrode assembly 550 is formed from an electrically-conductive material, defines a hollow interior 574, and includes an insulative sleeve 580 disposed about a portion of the external surface thereof. Needle 570 further includes a color-change material or color-change coating 590 disposed on at least a portion of inner surface 592 of needle 570 that defines hollow interior 574. Color-change coating 592 is configured to change from a first color, as shown in FIG. 6A, to a second color, as shown in FIG. 6B, although color-change coating 592 (or from the first color to one or more intermediate colors and, ultimately, to the second color) upon contact with one or more fluids, e.g., cooling fluid, may be temperature-sensitive, chemically-sensitive, electrically-sensitive, light-sensitive, and/or may otherwise be configured to selectively transition from the first color to the second color (and one or more intermediate colors therebetween) upon occurrence of a pre-determined event or condition. Color-change coating 590 may alternatively or additionally include time-sensitive features such that color-change coating 590 is changed from the first color to the second color, for example, upon exposure to one or more fluids, a pre-determined temperature, etc., for a pre-determined amount of time.

As an alternative to color-change coating 590, needle 570 may include any other suitable material, member, component, or assembly disposed within hollow interior 574 thereof that is configured to transition from a first state to a second state upon occurrence of a particular condition whereby the first and second states of the material, member, component, or assembly are differentiably detectable by an optical sensor 545.

With continued reference to FIGS. 6A-6B, handle assembly 510 further includes an optical sensor 545 disposed therein and positioned adjacent to needle electrode assembly 550 when needle electrode assembly 550 and handle assembly 510 are engaged to one another. Optical sensor 545, upon activation, monitors the color-change coating 590 disposed on inner surface 592 of needle 590 and transmits a response to control circuitry 540 of handle assembly 510 and/or to the control circuitry of generator 20 (FIGS. 1-2) based upon the optical properties, e.g., the color, of color-change coating 590. Control circuitry 540 (and/or the control circuitry of generator 20 (FIGS. 1-2)) analyzes the response received from optical sensor 545. More specifically, control circuitry 540 of handle assembly 510 (and/or the control circuitry of generator 20 (FIG. 1)) may include a memory 542 configured to store one or more acceptable response values, e.g., the response values corresponding to the first color and any intermediate or other acceptable colors colors, and/or one or more unacceptable response values, e.g., the response value corresponding to the second color, for comparison to the response received from optical sensor 545 to determine whether use of needle electrode assembly 550 is permitted and, thus, to determine whether to supply electrical energy and/or cooling fluid to needle electrode assembly 550.

The assembly and operation of ablation device 500 is similar to that of ablation device 200 (FIGS. 3A-3B) and, thus, only the differences therebetween will be described in detail below while similarities will be summarily described or omitted entirely. Initially, color-change coating 590 of needle electrode assembly 550 defines the first color, as shown in FIG. 6A. Upon engagement of needle electrode assembly 550 with handle assembly 510, optical sensor 545 is activated to sense the optical properties, e.g., color, of color-change coating 590 disposed on inner surface 592 of needle 570 and to transmit the detected response to control circuitry 540 of handle assembly 510 (and/or the control circuitry of generator 20 (FIG. 1)). Control circuitry 540 compares a response value of the response with the stored response values stored in memory 542. Since color-change coating 590 defines the first color in the condition of FIG. 6A, of which the corresponding response value is stored in memory 542, control circuitry 540 accepts needle electrode assembly 550 and may indicate that the needle electrode assembly 550 is accepted, e.g., via activating an LED (not shown) disposed on handle assembly 510 or providing an appropriate signal to generator 20 for display. The accepted needled electrode assembly 550 may then be used to ablate or otherwise treat tissue similarly as described above.

The circulation of cooling fluid through hollow interior 574 of needle 570, the supply of electrosurgical energy to needle 570, heat, chemicals, and/or any other suitable occurrence during use (or during sterilization after use) of needle electrode assembly 550 transitions color-change coating 590 from the first color to the second color (or the next incremental intermediate color), as shown in FIG. 6B.

Referring now to FIG. 6B, upon subsequent attempted use of needle electrode assembly 550, optical sensor 545 once again senses the color of color-change coating 590 and transmits the detected response to control circuitry 540. Since the response value corresponding to the second color is not one of the acceptable response values stored in memory 542 (and/or is one of the unacceptable response values stored in memory 542), needle electrode assembly 550 is rejected, and use of needle electrode assembly 550 is inhibited.

As can be appreciated, optical sensor 545, in conjunction with control circuitry 540 and color-change coating 590, inhibit re-use of needle electrode assembly 550 when color-change coating 590 defines a particular color or colors. Accordingly, depending on the configuration of color-change coating 590, e.g., depending on what occurrence(s) effect transitioning of color-change coating 590 to define one of the unacceptable color(s), use of needle electrode assembly 550 may be subsequently inhibited after single use, a pre-determined number of uses, or a pre-determined amount of use time. With respect to multiple-use needles electrode assemblies, color-change coating 590 may transition between the first color, one or more intermediate colors, and the second color. In such an embodiment, control circuitry 540 and optical sensor 545 may be used to not only determine whether needle electrode assembly 550 is acceptable, but may also indicate the number of remaining uses or time of use left, which is determined by the particular color defining color-change coating 590.

Further, optical sensor 545 and corresponding control circuitry 540 may be configured to inhibit use of a bent, deformed, or otherwise damaged needle electrode assembly, e.g., needle electrode assembly 450 (FIG. 5). In particular, color-change coating 590, a portion thereof, or a second color-change component (not shown) may additionally or alternatively be pressure-sensitive, thus changing color upon a change in stress or pressure applied thereto. Accordingly, if the needle electrode assembly is bent, deformed, or otherwise damaged, e.g., as is needle electrode assembly 450 (FIG. 5), the portion of color change coating 590 adjacent the bent, or damaged portion thereof would change color, thus indicating an abnormal or pressure or stress exerted on needle 570. This color-change may be sensed by optical sensor 545, thus indicating that the needle 570 is damaged and cannot be used. Accordingly, damaged needles can be inhibited from being used, even where there are uses remaining or where the use time limit has yet to expire.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a reusable handle configured to connect to a source of energy;
    a limited-use needle assembly releasably engagable with the reusable handle, the limited-use needle assembly including a needle body defining a hollow interior, the needle body transitionable from a first state, wherein the needle body defines a first frequency, the first frequency being a natural frequency of the needle body, to a second state, wherein the needle body defines a second frequency different from the first frequency; and a detecting member disposed within the reusable handle and configured to determine the state of the needle body, wherein the detecting member is configured to emit an acoustic signal into the hollow interior defined by the needle body and detect the state of the needle body based on a response to the emitted acoustic signal, wherein energy is permitted to be supplied to the limited-use needle assembly when it is determined that the needle body is disposed in the first state, and wherein energy is inhibited from being supplied to the limited-use needle assembly when it is determined that the needle body is disposed in the second state.

2. The surgical instrument according to claim 1, wherein the limited-use needle assembly is configured to supply energy to tissue to ablate tissue.

3. The surgical instrument according to claim 1, further comprising control circuitry disposed within the reusable handle and including a memory configured to store the first frequency, the control circuitry configured to receive the detected frequency from the detecting member and to compare the detected frequency to the first frequency stored in the memory for determining the state of the needle body.

4. The surgical instrument according to claim 1, wherein the response to the emitted acoustic signal is a standing wave correlated to a natural frequency of the needle body.

* * * * *